United States Patent [19]

Maschhoff et al.

[11] Patent Number: 5,272,627
[45] Date of Patent: Dec. 21, 1993

[54] DATA CONVERTER FOR CT DATA ACQUISITION SYSTEM

[75] Inventors: Robert Maschhoff, Cedar Crest; Kyong H. Lee, Albuquerque, both of N. Mex.

[73] Assignee: Gulton Industries, Inc., East Greenwich, R.I.

[21] Appl. No.: 676,164

[22] Filed: Mar. 27, 1991

[51] Int. Cl.⁵ .............................................. G06F 15/00
[52] U.S. Cl. ........................ 364/413.15; 364/413.13; 364/413.14
[58] Field of Search ....................... 341/143, 162, 163; 364/413.13, 413.14, 413.15, 565, 566, 571.05

[56] References Cited

U.S. PATENT DOCUMENTS

| | | | |
|---|---|---|---|
| 4,259,721 | 3/1981 | Kuznia | 364/413.15 |
| 4,521,115 | 6/1985 | Higginbotham et al. | 356/432 |
| 4,527,148 | 7/1985 | Kuboki et al. | 341/163 |
| 4,559,523 | 12/1985 | Wakita | 341/156 |
| 4,654,797 | 3/1987 | Fujita et al. | 364/413.21 |
| 4,670,852 | 6/1987 | Masaki et al. | 364/565 |
| 4,771,267 | 9/1988 | Russell, Jr. et al. | 341/118 |
| 4,894,778 | 1/1990 | Matsumura | 364/413.15 |
| 5,041,921 | 8/1991 | Scheffler | 360/13 |
| 5,105,194 | 4/1992 | Mizunoue | 341/156 |

Primary Examiner—Roy N. Envall, Jr.
Assistant Examiner—Stephen Tkacs
Attorney, Agent, or Firm—Darby & Darby

[57] ABSTRACT

A data acquisition system employs data conversion circuitry well suited to large multisensor systems such as computerized tomography systems utilizing X-ray detectors. The data conversion system consists of a number of detectors or similar signal sources and a corresponding number of data registers and accumulation registers. Each data register contains a previous sample output of a signal source. Differential data conversion is employed such that the difference between the previous output and the current signal source output is added to the data register in order to update it to the current signal source output. Each signal source is repeatedly sampled and the samples accumulated in an accumulation register. The data conversion system thus provides increased system linearity, accuracy, and dynamic range, and yields improved measurement simultaneity of a large number of signal sources. These factors combine to result in substantial improvement in image resolution after suitable processing by a computer. Increased resolution and dynamic range is achieved through oversampling and a differential data conversion technique, which may be implemented at relatively low cost with largely conventional components.

16 Claims, 4 Drawing Sheets

DATA CONVERTER FOR CT DATA ACQUISITION SYSTEM

BACKGROUND OF THE INVENTION

1. Field of the Invention

This invention relates to improved data converter circuitry for use in a computerized tomography (CT) or similar radiation imaging data acquisition system.

2. Background Information

Computerized tomography equipment, such as CT scanning apparatus, is widely used as a diagnostic tool for analyzing the internal profile of an object under study, such as for the medical diagnosis of a human body organ. Such equipment can provide a two or three-dimensional composite "picture" of the object by analyzing a plurality of radiation images taken of the object at different orientations. As is usually the case in medical and biomedical diagnostic technologies, improved image resolution and system speed are viewed as desirable objectives. Improved image resolution is directly related to the quality and reliability of medical diagnosis and may permit examination of fine structures previously not capable of being seen by X-ray imaging. Faster system operation tends to reduce the length of time for which a patient must remain essentially motionless, without which clear images cannot presently be obtained. For example, as much as thirty to forty-five minutes may be required with the use of current equipment to collect sufficient data to image just the lower lumbar or spinal region of a patient.

Another important use of CT scanning apparatus is in the field of bomb or explosives detection, such as the detection of explosives located within a suitcase or other piece of luggage destined to be loaded onto an airplane or other passenger vessel. It has been found that thermal neutron analysis (TNA) equipment, once viewed as an attractive solution to the problem of screening "checked" baggage, often provides an excessive number of false detections when attempting to detect small amounts (e.g., less than one pound) of plastic explosive material. In one recently reported study, CT scanning apparatus was demonstrated to more reliably detect such small amounts of concealed explosives. The screening rate (number of bags per hour) has thus far been unacceptable from a practical standpoint, however; a particular need thus exists in this area for faster CT scanning equipment, with higher image resolution.

A usual source of imaging radiation is a source of X-rays located on one side of the object, with the images being developed by one or more X-ray detectors located on the opposite side of the object, whose signal outputs are converted into digital signals which are analyzed by computer. In general, the CT data acquisition system receives the output from the detectors, and, under digital control to correlate a particular signal with a particular orientation, conditions, amplifies and converts the detector output signals into useful digital data form suitable for subsequent analysis.

Typical data acquisition circuitry has four main components: a front-end signal conditioner, an analog signal multiplexer, a data converter, and a digital control. The front-end signal conditioner serves to convert relatively low level analog signals from the detectors, typically photodiodes in state-of-the-art equipment, into low output impedance signals for the rest of the acquisition system. Normally, each detector channel or line has at least some dedicated signal conditioning circuitry associated with it.

The function of the conventional multiplexer is to take the signals from the different detector channels and enable them to be processed (in time-sharing fashion) along common channels, thereby reducing the number of components needed in the follow-on circuitry. It is known to those skilled in the art that the detector channels may be representative of either instantaneous readings or integrated values. In the former case, a track-and-hold capacitor is "read" without being discharged, while in the latter, a sampling capacitor accumulates charge between sample times and is zeroed after each reading.

The analog output of the multiplexer is fed into a data converter to transform the analog signals into corresponding digital signal information appropriately converted to digital form. The whole process operates under the direction of the digital control circuitry.

The data acquisition circuitry of conventional high performance CT systems utilizes more than one data converter because of the combined sampling rate and accuracy requirements. The data converter is often comprised of two primary elements, a floating point amplifier and an analog-to-digital (A/D) converter. To ensure that the input to the A/D converter is always greater than some minimum value, the floating point amplifier operates to provide greater amplification for smaller magnitude input signals, with the amount of amplification given to a particular signal being selected as a function of the magnitude of the input signal.

A prior art approach to data conversion circuitry utilizes a programmable or selectable gain amplifier in which gain is set by changing the feedback path through switching the point of connection to a plurality of resistors connected in series between input and output terminals of the amplifier. Because this approach achieves different gains by varying the feedback resistance of the same amplifier, the settling times are long and different for each gain selection. Also, implementation of an offset drift correction (auto-zero) capability is complicated and cumbersome, as each gain configuration requires a different amount of offset or offset value. Furthermore, gain adjustment is complicated because the same resistors affect more than one gain selection.

A second approach found in the prior art utilizes a plurality of amplifiers in parallel, each configured for a different single gain setting, and means for selecting which one of the amplifier paths will be used to amplify a given signal. This approach is faster than the first approach but requires a different amplifier, with a corresponding different settling time, for each gain setting. Also, because separate amplifier configurations are used, each gain setting will require its own auto-zero setting circuitry for offset voltage correction.

Still a third prior art approach to data conversion circuitry can be seen in Acharya et al. U.S. Pat. No. 4,815,118 for "Data Converter For CT Data Acquisition System." There, programmable gain amplifier circuitry having a switchable resistor attenuator stage is followed by a fixed amplifier stage, with gain being selected by varying the configuration of the resistor attenuator stage. A single settling time independent of gain setting is provided, enabling the simple implementation of an auto-zero feature.

In present state-of-the-art CT scanning equipment, on the order of five hundred individual photodiodes are used to provide relatively high resolution images of the body organ or structure under X-ray examination. Increased image resolution in such equipment is tied to the number of photodiodes or detectors employed; thus, it would be expected that one should simply scale up the number of photodiodes, along with the necessary supporting circuitry, in order to obtain better CT performance. Those skilled in the art recognize, however, that increased image resolution requires increased system linearity and dynamic range. None of the aforementioned prior art data conversion circuitry approaches are readily capable of practical and economical use in CT scanning apparatus which provides, for example, twice the image resolution as compared to currently available equipment.

Accordingly, it is an object of the present invention to provide computerized tomography apparatus having improved image resolution. A more specific object is the provision of data converter circuitry for use in CT scanning equipment having more than double the number of X-ray detectors than in present state-of-the-art equipment.

Another object of the invention is to provide CT scanning equipment having vastly superior performance characteristics with largely conventional, relatively low-cost components.

Additional objects and advantages of the invention will be set forth in the description which follows, and in part will be obvious to those skilled in the art from the description itself, and further in part will be appreciated by those practicing the invention and using the resulting CT scanning apparatus.

SUMMARY OF THE INVENTION

The present invention provides an improved data converter for a CT data acquisition system in accordance with the purposes of the invention. A presently preferred data converter is provided for CT imaging apparatus having 1,120 individual photodiodes, each photodiode representing one "channel." These X-ray detectors are arranged (electrically) in "modules" or groups of sixteen channels each, for a total of seventy modules. The modules are identical.

Individual transimpedance amplifiers are used at each photodiode input, eliminating deficiencies in dynamic range, linearity and crosstalk performance as compared to multiplexed front ends. Such prior art multiplexed front ends, including switching elements for readout and discharge on the photodiode output, are generally viewed as having dynamic ranges limited to about 80 dB.

The technique of "oversampling" is used to enhance dynamic range or signal-to-noise ("S/N") performance holding bit resolution constant, in a manner similar to that employed in digital audio reproduction. By increasing the oversampling ratio to, for example, sixteen times the upper band limit of the signal, the successive samples are seen to have a high dependence on past samples. This enables establishing a highly accurate, "slowly" varying "signal backbone," about which detail variations can be sampled and difference encoded. This technique permits achievement of a very large overall dynamic range and excellent linearity without costly high-performance analog-to-digital converters. Moreover, at sixteen times oversampling, concern over sampling-induced errors are dramatically reduced, since the input signals are being sampled at sixteen times the minimum rate or Nyquist rate (the Nyquist rate being twice the highest frequency of the input signal).

The "slowly" varying signal backbone exists as the contents of a dedicated "DAC" register. Each module contains sixteen such DAC registers, one per channel. After initialization, the DAC registers contain the last sample value for each channel to a resolution of, say, for example, 16 bits. This provides a significant advantage when a next sample is to be taken, with respect to the conversion process.

An accumulation register is also provided for each channel. The contents of the DAC register is added to the accumulation register each time the DAC register is updated. For 16-bit DAC registers, with 16 samples per summation window, keeping the entire number of bits results in a 20-bit sum. This integral representation is much more accurate than forming an analog integral as a voltage on a sampling capacitor and then digitizing that capacitor voltage.

This arrangement according to principles of the invention eliminates the limitation on dynamic range which is caused by the prior art use of sampling capacitors which must be discharged between successive readings. Because the best known dielectric absorption coefficients (the fraction of voltage which reappears after discharge) are about 0.01%, detection of extremely small values, or zero readings, are most problematic. The unavoidable consequence of the dielectric absorption coefficient is a limitation on the dynamic range to about 80 dB. A discussion of such errors appears in Wegmann et al., *Charge Injection in Analog MOS Switches*; IEEE J. Solid State Phys., SC-22:1091-97 (1987).

The problem of channel-to-channel crosstalk is also exacerbated when such sampling capacitors are used in a multiplexed or time-sharing arrangement in an effort to reduce the number of capacitors required.

A dedicated "track-and-hold" capacitor may be used to provide an integrated signal for each channel, as mentioned above. Such use of dedicated track-and-hold circuitry is shown in, e.g., U.S. Pat. No. 4,583,240 to Gatten et al., for Data Acquisition Circuitry For Use In Computerized Tomography System, wherein each data channel includes a 0.01 $\mu f$ polyester film integrating capacitor. That disclosure, however, merely solves the problem of channel-to-channel crosstalk, and does not address the limitations inherent in the use of capacitors.

However, in the present invention each module would require sixteen high quality, expensive capacitors. The DAC registers effectively provide an analogous function as much lower cost.

An interpolation process is employed so that, in effect, 32 samples are obtained for each accumulation period. Because of the high degree of oversampling employed, simple linear interpolation between the actual samples taken at the input is extremely accurate.

BRIEF DESCRIPTION OF THE DRAWINGS

A preferred embodiment of the invention is illustrated in the accompanying drawings, wherein.

DETAILED DESCRIPTION OF THE PREFERRED EMBODIMENTS

Figure 1:
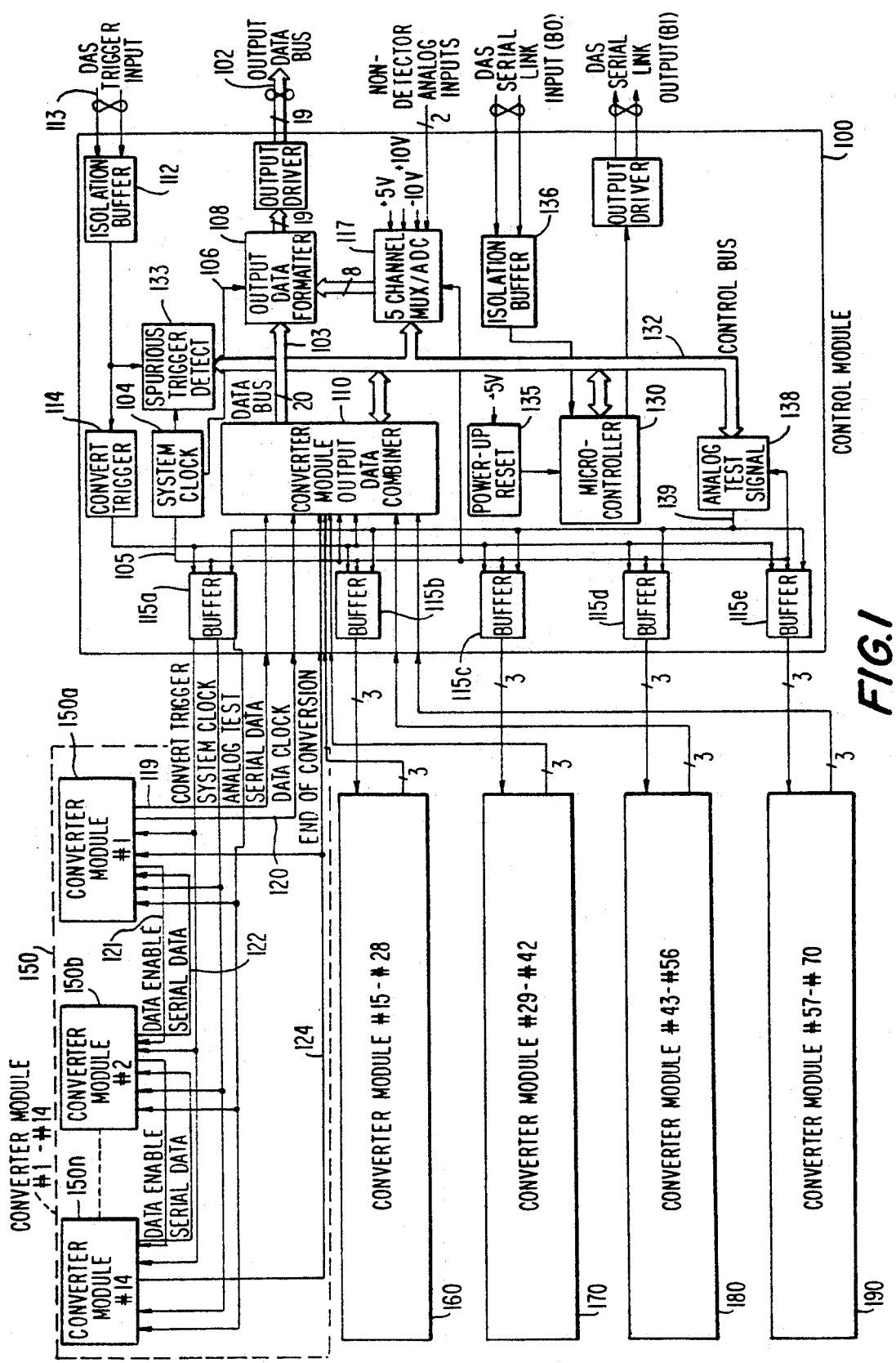
FIG. 1 is a block diagram of a data acquisition system for use in computerized tomography equipment.

A presently preferred data acquisition system ("DAS") for CT scanning equipment is shown in FIG. 1. The DAS control module 100 broadly performs all data handling and control functions necessary to obtain CT data via five strings of fourteen converter modules each (150,160,170,180,190), and to combine, format and deliver that CT data to the system computer (not shown) over the output data bus 102, for further analysis and processing. The strings are identical, as are the fourteen converter modules within each string. Each converter module (150a, 150b, . . . ,150n) comprises sixteen channels, yielding a total of 1,120 data channels in the preferred DAS. The preferred typical converter module according to principles of the invention will be described in detail in connection with FIGS. 2 and 3.

Referring again to the control module 100 of FIG. 1, a system clock 104 preferably comprises a very accurate free-running crystal oscillator operating at, for example, 21.84 Mhz. Divide-by circuitry may be included to generate the 5.46 MHz system clock signal 105 and the faster 10.92 MHz clock signal 106 required by the output data formatter 108. It will be understood that details such as clock signal frequencies may be varied without departing from the spirit or scope of the invention.

It is important, however, that the system clock signal 105 should be as fast as can be safely designed in accordance with sound digital circuit design practices. More particularly, any given design should take into account considerations of driving the various clock signals up and down the interconnect cables, and of guaranteeing data and clock coherency where digitized data are returned to the converter module output data combiner 110. Sound design practices call for the use of individual buffer drivers (115a, . . . , 115e) between the control module 100 and each of the converter module strings (150, . . . , 190), as well as between the convert trigger signal 114 and the strings.

In operation, data are output simultaneously in serial form from each string to the output data combiner 110. In the detailed discussion below concerning the converter modules, the ping-pong operation of the 20-bit accumulation registers is explained. There it will be seen that data from each input channel are oversampled by a factor of 16 and accumulated during one view period and are then output serially during the next view period. As a result, almost an entire view period (as defined by successive DAS trigger inputs 113) is available for output of the data sampled during the previous view period. It is also necessary to allow a small amount of time to incorporate the data from the 5-channel mux-/ADC 117 of the control module 100 onto the output data bus 102. For the presently described embodiment, a serial data output rate of 5.46 MBPS from each converter module string is achieved.

The 5.46 MHz system clock signal 105 (routed to all of the converter modules) therefore establishes the serial data output rate as well as the data clock which accompanies this serial data back to the control module 100. This data clock signal 105 is the same signal which actually transfers the serial data from the first converter module in each string (e.g., converter module #1 (150a) in the first string 150) out to the control module 100. As a result, the serial data from each string are shifted into the output data combiner 110 by a coherent clock signal, as already mentioned hereinabove.

At the start of each view period, as defined by the convert trigger 114 (i.e., the DAS trigger input 113 synchronized to the 5.46 MHz system clock signal 105), the accumulator data for channel #1 of the first converter modules in each string (i.e., modules #1, #15, #29, #43 and #57) are loaded into an output register (not shown) and serially shifted out by its respective data clock 120. This operation is successively repeated for each of the 16 channels of each converter module to form a continuous serial data output from each converter module (e.g., serial data 119).

At the start of the sixteenth channel output of the first converter module 150a, the module 150a generates a data enable signal 121 back to the second converter module 150b in the string 150. This initiates the same sequence of data output operations in this second converter module 150b. Its serial data 122 are routed through the output register on the first module 150a to hook up with the latter's last data word so that the data remains continuous between converter modules. This series of sequential serial data output operations is repeated down each string to the last (fourteenth) module, forming a continuous 5.46 MBPS output for the 224 (14×16 =224) 20-bit data words produced by each string. The data stream for each view period is terminated by the end of conversion signal 124 which is derived from the data enable output from the last converter module (e.g., 150n) in each string.

In addition to initiating this data output operation for data sampled and accumulated during the previous view period, the convert trigger 114 also initiates the accumulation operations for the current view period. The 5.46 MHz system clock signal 105 provides the time base for these operations as well as the on-going sampling operations.

It should be noted here that the sampling operations are continuous and overlap view period boundaries, whereas the accumulations per view period are discontinuous from one view period to the next. The timing and control of the accumulation process is arranged so that all 16 channels in any given converter module, and all channels in the overall DAS system, receive the same number of accumulations in a given view period.

In the control module 100, the serial data from the five converter module strings (150, . . . , 190) are combined by the output data combiner 110 and unloaded in successive 20-bit parallel words at a 1.37 MHz word rate, in this presently preferred embodiment of the invention. The output data combiner 110 consists of serial/parallel input registers under control of the input data clock (e.g., 120) from each of the five converter module strings. The data are preferably double-buffered at the word rate of each individual string (273 KHz) and then sequentially output from the five tri-state buffer registers at the 1.37 MHz system word rate. The gated data clocks 120 are implemented to derive the 273 KHz load signal such that data word coherency is maintained in the serial-to-parallel data conversion process.

The data are output in simple sequential order starting with the first module string 150. The output data formatter 108 performs real time compare-and-shift operations to convert each 20-bit binary word into a 14-bit binary mantissa and 2-bit exponent equivalent form in real time so that the data order on the output data bus 102 is the same as that received on the internal data bus 103 from the output data combiner 108. The exponent can be either a base 4 or a base 8 format as required. Due to the number of shifts that could be required in the base 4 format, the 10.92 MHz clock signal is implemented to complete each operation within the 730 $\eta$sec available at the 1.3 MHz output data word rate.

As thus described, the detector data order on the bus 102 will be as follows:

CM (converter module) #1 CH (channel) #1, CM #15 CH #1,

CM #29 CH #1, CM #43 CH #1, CM #57 CH #1, CM 1 CH #2,

CM #15 CH #2, . . . . , CM #14 CH #16, CM #28 CH #16, CM

42 CH #16, CM #56 CH #16, CM #70 CH #16.

Immediately following CM #70 CH #16 will be the five data words from the 5-channel mux/ADC 117 which samples the three power supply lines and the two external non-detector analog inputs. The mux/ADC 117 is preferably configured as a single-tier X followed by a buffer amplifier and flash ADC. The X may be stepped through at a relatively slow rate at the start of each view period, with the 8-bit ADC output for each of the five channels being stored in output registers. This allows adequate settling time for each channel. The data are then read out of each of the five registers sequentially immediately following the output of the last detector channel data word. These sampled signals are also routed through the output data formatter 108 and can be output in any order desired.

When the data are so ordered and combined, it is advantageously left to the CT system computer to order the data sequence as required, making this a software, rather than hardware, function.

The micro-controller 130 of the control module 100 is designated for control functions only and is not directly involved in the data handling operations. The micro-controller specification will be understood to be adapted to the particular hardware and software requirements of the CT scanning equipment. The detail design and implementation of this industry standard micro-controller 130 is deemed a routine matter for one of ordinary skill in the art.

It should be noted here that the micro-controller 130 is preferably not included in the data handling path primarily because of the speed of operations which would be imposed thereon. Additionally, in a DAS according to the invention, it is not difficult to control the data directly with logic. This permits dedication of the micro-controller 130 to control functions only, which, if not excessive, can be handled with a PROM and RAM internal to the micro-controller 130. The INTEL 8751 micro-processor is suitable for this application as it includes an internal EPROM and RAM as well as a serial input port for an RS-422 input.

Control functions to be provided by the micro-processor may include the following:

1) Initiate one view of data sampling and output in response to each DAS trigger input.

2) Detect and notify the CT system computer in the event of a premature spurious DAS trigger pulse on the trigger input line 113.

3) Implement a DAS serial link input signal (B0) for command or setup information and to query the DAS about its status and initiate self-test.

4) Implement the DAS serial link output signal (B1) to supply status information upon request via the B0 input.

5) Reset to standby mode and be ready to receive prescan instructions in response to power-up or a momentary power-off transient.

The DAS trigger input pulse is preferably received via an isolation buffer 112. The trigger pulse is then synchronized to the system clock signal 105 to produce the convert trigger 114 which is routed to all of the control modules, as discussed above, to initiate one view of data sampling and output.

The spurious trigger detect circuit initiates a timer in response to each DAS trigger input pulse. If a second DAS trigger pulse is received before this timer (which counts to the minimum view period interval) times out, a flag is set which is reset only in response to a status request either from an internal interrupt or from the CT system computer. Appropriate investigative or corrective action may be taken in response to the set flag.

The DAS serial link input signal B0 may, for example be a 9600 baud RS-422 asynchronous signal which is routed to the micro-controller serial input port from the DAS input isolation buffer 136. Appropriate command and setup information for the micro-controller are transmitted from the CT system computer in this manner. The B0 signal may also be used to initiate a self-test function whereby an analog test signal is injected into each detector signal input processing circuit. Thus the analog test signal block 138 is shown outputting an analog test signal 139 to all of the converter modules in response to an input from the control bus 132. When this circuit is activated (and the detector inputs are inactive) the DAS trigger pulses initiate view periods in which the value of each converter module channel input is known. This self-test data is sampled and output just the same as if it were detector data and is output via the same output data bus lines 102.

The DAS serial link output signal B1 is available for additional status information beyond that supplied by the self-test operation described above, as may be desired.

Finally, the power-up reset function 135 is readily implemented with an RC charge circuit that applies a momentary ground to the micro-controller reset input when power comes up. In the case of a momentary power-off transient, it may be necessary to command a reset via the DAS serial link input signal B0.

Having thus described the circuit environment in which the converter module of the invention resides, the structure and operation of the converter module will now be described with reference to FIGS. 2 and 3. The circuitry shown in FIG. 2 will be understood to represent a single one of the seventy identical converter modules of the DAS.

Figure 2:
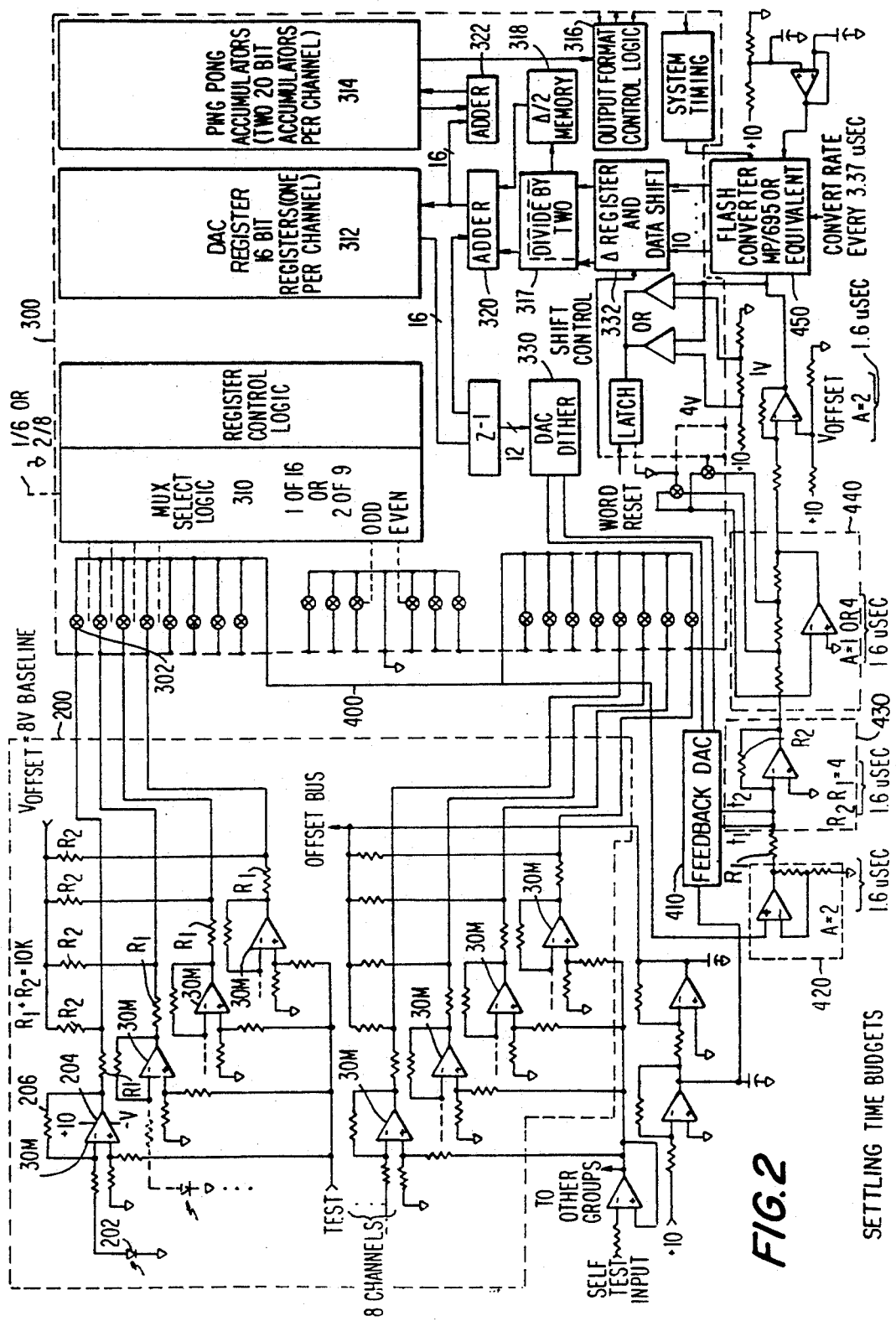
FIG. 2 is a simplified schematic and block diagram representation of a sixteen-channel converter module for use in the FIG. 1 data acquisition system.

A converter module such as converter module 150a of FIG. 1 comprises a detector/amplifier functional block 200 interfaced with a logic/processing functional block 300, and certain additional discrete componentry, referring now to FIG. 2. In the detector/amplifier block 200, an individual transimpedance amplifier 204, which may suitably be a JFET input amplifier, is employed as the interface with the X-ray detecting photo-diode 202. The LINEAR TECHNOLOGY LT1058 device is well-suited to this application given the need for exceptionally low signal-to-noise ratios and device power considerations, because of the multiplying factor of sixteen amplifiers per module Each converter module includes sixteen transimpedance amplifiers connected to sixteen respective photodiodes, each photodiode/amplifier representing one of the 1,120 data channels of the DAS according to the invention. This design approach avoids known limitations in dynamic range and linearity which are attendant to various prior art approaches using multiplexing at the detector/amplifier interface.

As will be described in greater detail hereinbelow, all of the logic functions and channel selection functions required for subsequent time sharing are suitably executed on a single Application Specific Integrated Circuit (ASIC), preferably coextensive with the illustrated boundary of logic/processing functional block 300.

The sixteen data channels of the detector/amplifier block 200 are advantageously arranged in groups of four channels centered around a quad operational amplifier package. The four channel grouping is then repeated four times, with only the first and fourth grouping being shown in FIG. 2. It will be readily understood by those skilled in the art that this amplifier circuit arrangement is essentially conventional.

An important aspect of proper operation of the amplifier circuit, however, is the selection of an appropriate feedback resistor 206 to achieve suitably low transimpedance amplifier noise. The resistor value depends on the desired full scale output of the amplifier 204, the resistance and capacitance values of the photodiode, and the operating characteristic of the particular amplifier selected. Also, types of resistors which exhibit excessive noise generation, such as carbon type, must be avoided. A preferred example is as follows:

---
$R_t = 30$ M; $R_d = 30$ M; $C_d = 300$ pf; $F_n = 578$ Hz;
Op amp noise density (worst case, LT1058) = 24 nV/$\sqrt{Hz}$;
1/f corner frequency = 28 Hz.
Current noise:
photodiode = $0.575 \times 10^{-12}$
resistor = $0.575 \times 10^{-12}$
op amp = $0.376 \times 10^{-12}$
Total current noise = $0.896 \times 10^{-12}$
Noise level/full scale signal = 1.95 ppm
Full scale signal output = 13.800 V
S/N [dB] = 114.2 dB
---

As noted above, the polarity of the signal current out of the photodiode 202 produces a negative output voltage at the amplifier 204. A level shifting divider (not shown) at the output ahead of the multiplexer translates that negative output voltage to a 0 to +5V range, without degrading S/N performance. Appropriate design of the level shifting divider also serves to minimize the effect on the amplifier 204 of transients which occur when the multiplexer switch closes. With the divider element impedance in the 5 kilohm range and the output impedance in the 50 ohm range, a first order decoupling of 100 to 1 occurs.

Finally with respect to the detector/amplifier block 200, a high ratio resistive divider network is included to inject the analog test signal 139 (produced by analog test signal block 138 of FIG. 1) into the non-inverting input of the transimpedance amplifiers. This exercises each input amplifier but advantageously does not require switching in the signal path. When the analog test signal voltage is zero there is no voltage drop across this resistive divider network and normal detector signals will not be affected, i.e., no crosstalk opportunity is introduced.

The channel select multiplexers 302 are located in the logic/processing functional block 300, preferably on the ASIC. In this preferred embodiment, the multiplexer control signals from the MUX SELECT LOGIC block 310 do not require long circuit runs and thus have little opportunity to capacitively or radiatively couple into the common signal line 400. An "on" resistance of about 500 ohms when coupled with the effective source resistance of 2 kilohms and a common bus capacitance of 25 pf yields a time constant of 75 $\eta$secs.

From the output of the multiplexer 302 on, all the circuitry external to the ASIC is time shared. FIG. 2 indicates baseline settling time budgets for the major off-chip functions. The majority of difference encoder building blocks are preferably executed off-chip for accuracy and repeatability reasons.

A key performance parameter is determined by the DAC used in the feedback loop. The feedback DAC 410 is the main determinant of system linearity over the required large dynamic range. When executed in dual form, linearity of 1 part in $2^{16}$ or better can be advantageously achieved over a dynamic range of $2^{16}$. Because the DAC functions can be provided to such a high degree of accuracy, the difference or ΔADC requirements (i.e., for the flash converter 450) in effect become more relaxed, allowing selection of a relatively low-cost device for that ΔADC function.

A 16-bit DAC register 312 is provided on the ASIC for each of the sixteen data channels of the converter module. The function of the DAC register 312 is to duplicate the analog input signal level at discrete points in time representing the sample times for each channel. The duplication is achieved by the DAC register 312 storing the digitized detector output sample signal that is present on its input bus 313, This duplication is to 16 bits of resolution and is consistent with the linearity provided by the feedback DAC 410.

Generally, when the time comes to obtain a new sampled data point from a particular channel, the most significant bits of the DAC register 312 are applied to the feedback DAC 410. If the new sampled signal level from the channel did not change since the previous sample time, the number in the DAC register 312 will not be changed as a result of the difference encoding (to be described in detail below). Conversely, if the signal level has changed then the difference encoding result will be added to the DAC register 312 contents, thus providing the required tracking function according to the invention.

A separate set of operations next takes the DAC register 312 contents and applies them to one of the two 20-bit ping-pong accumulators 314 provided for each of the sixteen data channels of the converter module. In one embodiment of the invention this would involve the accumulation over 16 samples. But in the presently preferred embodiment, in view of unavoidable timing jitters and the desire to improve simultaneity among all the channels in the DAS, an interpolation process is employed so that, in effect, 32 samples are required for each accumulation. Because of the high degree of oversampling employed, simple linear interpolation between the actual samples taken at the input is accurate to within 0.5%. Resetting the accumulator to zero after each readout eliminates view-to-view crosstalk.

The last step in this process, generally, is interfacing with the control module 100. The converter module uses clock and trigger information to transfer the accumulated data, via an output format control logic block 316, down the serial data line (e.g., line 119 from converter module #1 (150a)) to the output data combiner 110, as shown in FIG. 1.

The digitizing process will now be described in detail in connection with FIGS. 2 and 3. In the presently preferred embodiment, an average view period (for all channels of a single converter module) of 865 $\mu$sec is provided. To support an over-sample ratio of 16:1 and also time share the digitizing circuitry among 16 channels yields a nominal per sample interval of 3.37 (865/256) $\mu$sec.

Figure 3:
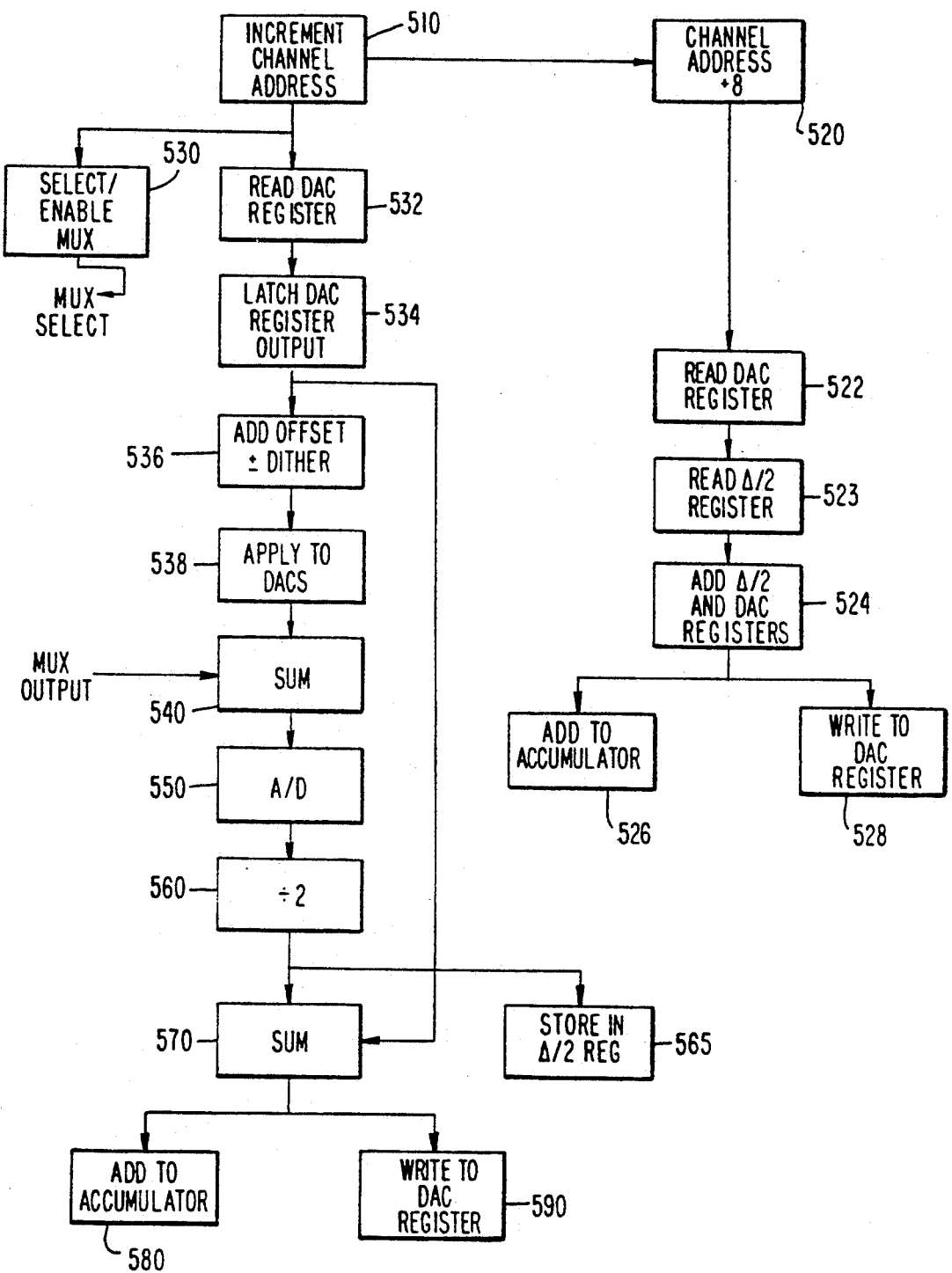
FIG. 3 is a numerical flow diagram illustrating the stepwise operation of one channel of the converter module shown in FIG. 2.

All of the numerical step operations shown in FIG. 3 are completed within each 3.37 $\mu$sec sample interval. The 5.46 MHz system clock signal 105 provides 18 clock cycles in one sample interval. No more than about 8 clock cycles are required to perform all the necessary computations and register/RAM read/write operations described below.

The nominal per sample interval is manageable in view of typical semi-custom CMOS ASIC maximum switch turn-on times. This switch turn-on time needs to be kept as short as possible but yet just long enough to ensure that there is no temporary cross channel connection. Use of a break-before-make operation should be included in the control logic. With the control lines totally resident on the ASIC there is great flexibility in arranging this mode of operation. It is also seen that the multiplexer time constant of 75 $\eta$sec will support the 3.37 $\mu$sec sample time budgeted.

First, the channel address is incremented (step 510 on FIG. 3). The new incremented channel address is again incremented by 8 (step 520), with the N+8 address being used in the linear interpolation process. The incremented channel address (510) is read out (step 530) to select and enable the appropriate multiplexer channel. Conversion of the selected input is done at the end of the sample interval to allow for maximum settling time. The input multiplexer is enabled for the entire 3.37 $\mu$sec sample interval.

During the first half of the sample interval, the corresponding DAC register 312 is read (step 522), the $\Delta$/2 register 318 is read (step 523), and these registers are summed by an adder 320 (step 524), all for channel N+8. The sum is stored back into the DAC register 312 (step 526) and the ping-pong accumulator 314 then being loaded is updated as well for channel N+8.

As for channel N, the DAC register 312 is read (step 532) and the DAC register output is latched (step 534). The offset and appropriate dither amount are summed with the DAC register output (step 536). Generation of the dither amount by DAC DITHER block 330 will be described in greater detail below. The sum is applied to the feedback DAC 410 (step 538) and is converted to an analog current signal.

It should be noted that the dither amount is ultimately added back to the digitized value by adder 320 before rewriting an updated value to the channel N DAC register 312, so as not to introduce the dither amount as an initial data error.

The mux output on common line 400 is summed with the feedback DAC output (step 540) by a fixed gain differential amplifier 430. As explained further below in connection with the resolution requirements of the A/D converter 450, this amplified analog difference signal may be further amplified by a factor of either 4 or unity by variable gain stage 440.

Near the end of the sample interval, the amplified analog difference signal is applied to a parallel comparator flash-type A/D converter 450 and the signal is converted (step 550). This type of device has an aperture time of less than 100 $\eta$secs and will support a new conversion every 500 $\eta$secs.

The digital result is summed with the current channel N DAC register contents in block 320 (step 570). The digital result is also divided by two in block 317 and the quotient is stored in the sixteen channel $\Delta$/2 register 318 at channel N's address (step 565) for use during the sample of input channel N+8.

Finally, the sum is written back into the current channel N DAC register 312 (step 580) by the adder 320 and is also added to the accumulator 314 (step 590) by a second adder 322. The entire sequence of steps is then repeated, starting with incrementing the channel address (step 510).

Input sampling, as just described, is performed continuously without regard to the convert trigger 114 input status. The accumulator is cleared when the trigger pulse occurs. The trigger also switches ping-pong accumulators A and B from input to output and vice-versa.

As thus described above, a data converter for CT scanning apparatus is provided which has an overall dynamic range of $2^{20}$ and linearity of 1 part in $2^{18}$. The overall dynamic range of 20 bits results from an elemental area summation in the accumulator 314 where each element amplitude is known to 16 bits and there are 16 elements. At the 16-bit level the random noise will make the central limit theorem applicable yielding a noise floor at the 20-bit level. The following device resolution and linearity parameters are selected to achieve these overall system results.

It is seen that overall resolution of the data converter, represented by the bit resolution of the feedback DAC 410 plus the flash A/D converter resolution, must add up to 16 bits. The data converter satisfies a slewing requirement to go from zero to full scale 16 bits in two view intervals, involving 32 update samples. The required resolution is therefore $\pm 2^{11}$ (i.e., $2^{16}/2^5$). This leaves an absolute minimum resolution requirement for the feedback DAC 410 of $2^5$ (i.e., $2^{16}/2^{11}$). However, in a real slewing situation the DAC input might be just short of a boundary causing the next DAC step to be off nearly 2 bits out of $2^5$. By adding 5 bits to the above minimum requirement, the feedback will be within 3.12% of the value needed even during slewing. This yields a 10-bit DAC resolution requirement. Linearity of the feedback DAC 410 needs to be much better, and the device is linear to 14 bits in this preferred embodiment of the invention.

Directly providing the flash converter 450 (also called the $\Delta$ADC) with $\pm 11$-bit resolution may be done but is not cost effective with current technology and is therefore not presently preferred. Raising the sample rate to encompass 32 samples per integration interval rather than 16 is tractable but is also not presently preferred.

According to the preferred embodiment of the invention, a $\pm 9$-bit $\Delta$ADC can be used, in conjunction with the variable gain stage of 1 or 4 preceding the $\Delta$ADC 450. Normally the stage operates at a gain of 4 and the ADC output is properly justified to the LSB end of the 16-bit DAC register. During slewing or when the error might be larger, the gain is dropped to one and the ADC's output needs to be shifted left two bits by the data shift block 332 before addition to the DAC registers 312. This slightly degrades the resolution to 14 bits but only while following large transients. When the signal rate of change decreases to ¼ of the maximum tracking capability, full 16-bit resolution applies.

An alternative approach to using a low cost ΔADC is available in view of the high oversampling ratio. By storing the last difference as well as the cumulative total represented by the contents of the DAC registers, a linear prediction can readily be made. Rather than having the feedback DAC 410 provide a level as close as possible to the previous sample time signal level, it may be driven to a predicted value based on the last difference plus the last absolute level. At an oversampling ratio of 16:1, the maximum error in such a prediction for a sine wave at the Nyquist frequency is 20%. The maximum ΔADC signal range required is thus reduced by a factor of five. A ±9-bit ADC could then be used without gain switching in the error path.

Critical to large scale linearity is the feedback DAC 410, as noted above. According to the invention, it has been found that using two modest performance (i.e., 12-bit) DACs in concert is more effective than a single high performance (including high linearity) DAC. The DAC1220 12-bit binary multiplying D/A converter available from NATIONAL SEMICONDUCTOR is suitable for such use in the data converter according to the invention. The deposited thin film R-2R resistor ladder technology of the DAC1220 is most advantageously employed where all the ladder elements have the same accuracy tolerance as the MSB elements. An alternative device for this purpose is the HS7541 12-bit monolithic multiplying DAC available from HYBRID SYSTEMS CORP.

Typically the most critical point in a weighted current source DAC is the half scale point. If a half scale value is desired at the output, forming an average of full scale and zero will give a perfect result provided the offset is zero. Using two DACs and controlling one to produce full scale and the other zero will solve the half scale problem if their full scale contributions are equal as well. Even the full scale equality restriction can be lifted if a pair of excitations is set up so that first one DAC is at full scale and then the other. The DAC at zero would alternate as well. In the overall scheme this reversal would occur 8 times during a summation interval. This is the essence of the dithering function provided by DAC DITHER block 330.

Figure 4:
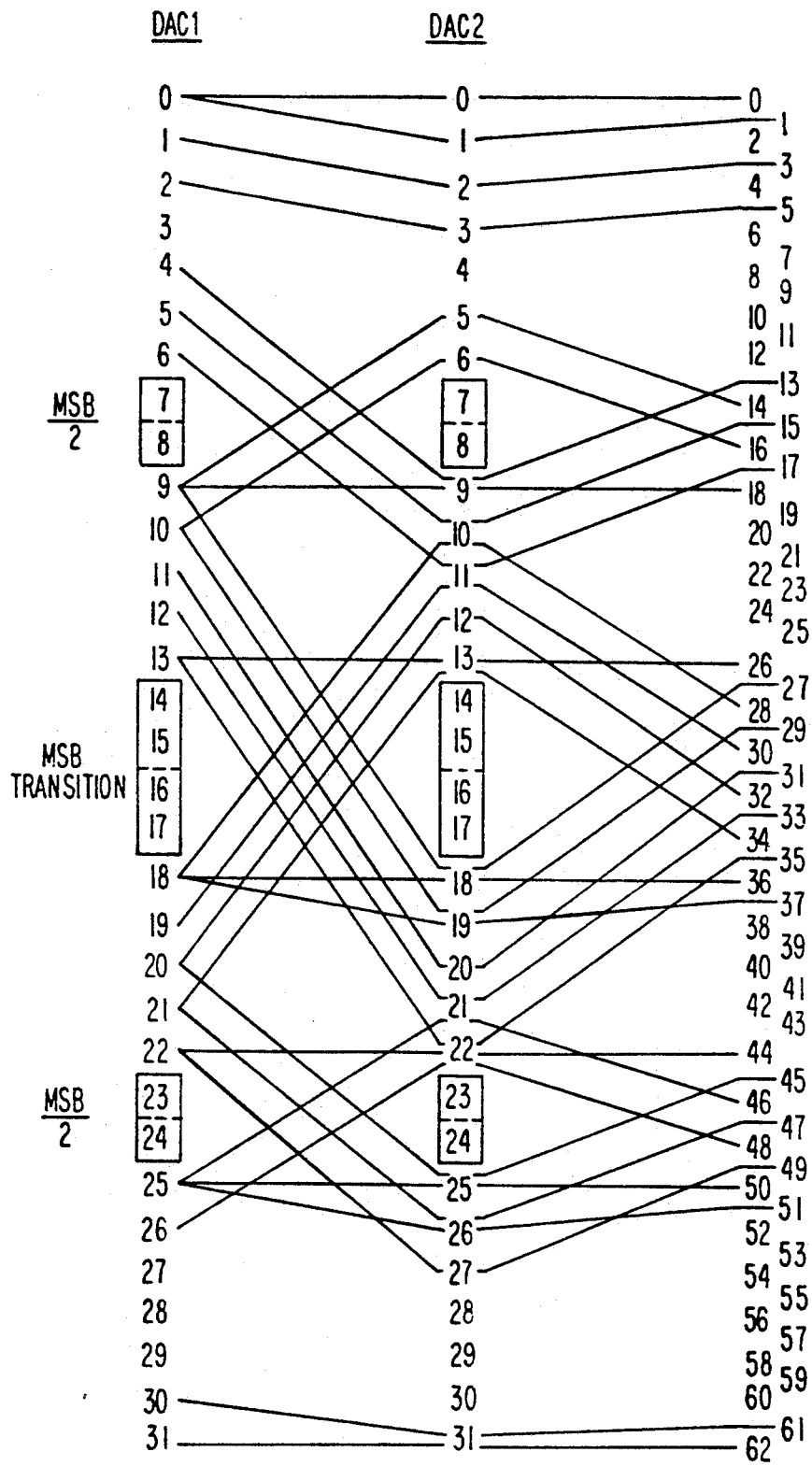
FIG. 4 is a diagrammatic representation of a dithering strategy for dual DACs in order to enable the use of lower cost components.

There are other points in the DAC transfer function that cannot readily be ignored such as the ¼ and ¾ scale points. A more general solution is to program the DACs according to a strategy shown in FIG. 4. The illustrated strategy avoids using codes near the major bit transitions. The strategy involves a maximum difference envelope at midscale and smaller differences at the ¼ and ¾ scale points. At the end points, improvement is neither necessary or possible. This strategy results in a linearity improvement equivalent to 1 bit.

Because there are at least 16 samples and therefore 16 pair opportunities per view, view-internal time averaging can be employed to improve this result. A different dither strategy is used for each pair. Averaging the effect of two strategies improves the linearity by a factor of 4. This provides increasingly better effective linearity as the signal frequency decreases. For large signal excursions the linearity will be at the 0.01% level using 12-bit DACs and the benefit of single pairing.

This advantageously allows use of a pair of 12-bit DACs executed on one monolithic chip. Being on one chip further enhances the synergism because matching linearity error patterns of the two DACs cancel more completely.

Read Only Memory (ROM) is preferably used as a look-up table for the DAC dithering function. This function could also less desirably be implemented with a register arrangement. The 12 most significant bits of the DAC register output are used to address to the ROM. Of those twelve, six are input to the dither process.

As is evident from the foregoing detailed description, the invention provides a dramatically improved data converter for a CT data acquisition system. Oversampling and linear interpolation techniques are employed to acquire and process data from more than double the conventional number of X-ray detectors. The data converter according to the invention uses relatively low-cost components to digitally "synthesize" more accurate processing functions. In performance, overall dynamic range of $2^{20}$ and linearity of 1 part in $2^{18}$ is achieved.

It should be apparent to those skilled in the art that various modifications may be made to the disclosed embodiments without departing from the spirit or scope of the invention, as limited only by the claims.

We claim:

1. A computerized tomography system comprising:
    a radiation source;
    a plurality of radiation detectors which provide detector output sample signals in response to receipt of radiation passing from the source through a tomography subject;
    a data converter connected to the radiation detectors and responsive to the detector output sample signals to produce digitized output signals for further signal processing; and
    a digital computer connected to the data converter to receive and process the digitized output signals so that they convey information about the tomography subject to a human being;
    the data converter comprising:
        a first storage register which receives and stores a first digitized sample signal derived from a first detector output sample signal from a first one of the plurality of radiation detectors the first digitized sample signal being sampled and digitized by an analog to digital converter;
        a feedback digital-to-analog converter, the converter having an input and output, the input being connected to the first storage register to provide a first analog feedback signal at the converter output corresponding to the first digitized sample signal stored in the first storage register;
        a difference amplifier responsive to the first analog feedback signal and a second detector output sample signal from the first one of the plurality of radiation detectors for providing at an output of the difference amplifier, a first difference signal corresponding to any change in value between the second and first detector output sample signals;
        digitizing means responsive to the output of the difference amplifier for digitally difference encoding the first difference signal; and
        means responsive to the digitizing means and the first storage register for providing a second digitized sample signal, the second digitized sample signal being the sum of the digitally difference encoded first difference signal and the first digitized sample signal, the second digitized sample signal also corresponding to the second detector output sample signal from the first one of the plurality of radiation detectors, and storing the second digitized sample signal in the first storage register.

2. The computerized tomography system of claim 1, the data converter further comprising:
a multiplexer for sequentially providing detector output sample signals from each of the plurality of radiation detectors to the difference amplifier, the multiplexer being adapted to connect each radiation detector to the difference amplifier at a rate faster than the rate at which the data converter provides digitized output signals corresponding to a given radiation detector for further signal processing.

3. The computerized tomography system of claim 2, wherein the data converter provides to the digital computer one digitized output signal for every sixteen detector output signal samples obtained from each radiation detector.

4. The computerized tomography system of claim 3, wherein the data converter provides to the digitized output signals for each radiation detector at the system Nyquist rate, thereby oversampling the radiation detectors by a factor of sixteen.

5. The computerized tomography system of claim 3, wherein an interpolation circuit divides the sixteen detector output signal samples into thirty two detector output signal samples.

6. The computerized tomography system of claim 2, wherein the data converter is adapted to provide to the digital computer one digitized output signal for a plurality of detector output signal samples obtained from each radiation detector.

7. The computerized tomography system of claim 6, wherein an interpolation circuit divides each of the plurality of detector output signals into $2^N$ individual samples, where N is an integer.

8. The computerized tomography system of claim 1, wherein the feedback digital-to-analog converter has a first and second input and a first and second output and comprises a first analog-to-digital converter connected between the first input and the first output and a second digital-to-analog converter connected between the second input and the second output;
the computerized tomography system further comprising a dithering module connected between the first and second inputs of the feedback digital-to-analog converter and the first storage register, the dithering module dividing a digital signal that is near a major bit transition into a first component above the major bit transition and a second component below the major bit transition, the first component being applied to the first input and converted by the first digital-to-analog converter and the second component being applied at the second input and converted by the second digital-to-analog converter.

9. For use in measuring signals in a multichannel radiation detecting system having a plurality of radiation detectors and corresponding radiation detector analog signal channels:
a plurality of digital storage registers, one per radiation detector;
first means for deriving a digital signal representative of an output of each radiation detector analog signal channel, without the use of discrete sample-and-hold circuitry; and
second means for storing each so derived digital signal in a respective one of the plurality of digital storage registers.

10. Apparatus according to claim 9, wherein the first means includes third means for providing a difference signal representative of a change in detector output from a first sample time to a next sample time, to a fourth means for adding the difference signal to the previously stored digital signal.

11. A data converter for a radiation imaging data acquisition system, comprising:
a plurality of detectors disposed opposite a radiation source to receive radiation from the radiation source after the radiation passes through an object to be radiation imaged, the object being between the plurality of detectors and the radiation source;
a plurality of detector amplifiers connected to the plurality of detectors, the plurality of detector amplifier outputs being selectably connectable to a detector signal sampling line, the detector signal sampling line being connected to one input of a difference amplifier;
first means for storing in a register a first digital signal representative of a previous detector amplifier output signal on the detector signal sampling line;
second means for providing an analog signal corresponding to the first digital signal to the other input of the difference amplifier, the difference amplifier providing an analog difference signal at its output; and
third means for converting the analog difference signal to a digital difference signal and updating the first means by storing therein a second digital signal representative of a updated detector amplifier output signal on the detector signal sampling line.

12. The data converter according to claim 11 further comprising:
fourth means for accumulating a predetermined number of digital signals sequentially stored in the first means.

13. The data converter according to claim 12 further comprising:
fifth means for providing to a digital computer, a digital detector output signal from the data converter each time a counter counts up to the predetermined number, the accumulated digital signals being representative of a total amount of radiation received by the detector over a time required for the counter to reach the predetermined number.

14. The data converter according to claim 11 wherein the detector is a photodiode.

15. The data converter according to claim 11 wherein the detector amplifier is a transimpedance amplifier.

16. For use in measuring signals in a multichannel data acquisition system having a plurality of data sources:
a plurality of digital storage registers, one per data source;
first means for deriving a digital signal representative of an output of each data source, without the use of discrete sample-and-hold circuitry; and
second means for storing each so derived digital signal in a respective one of the plurality of digital storage registers.

* * * * *